(12) United States Patent
Chokshi

(10) Patent No.: US 6,900,174 B2
(45) Date of Patent: May 31, 2005

(54) PHASEOLAMIN COMPOSITIONS AND METHODS FOR USING THE SAME

(75) Inventor: Dilip Chokshi, Parsippany, NJ (US)

(73) Assignee: Pharmachem Laboratories, Inc., Kearny, NJ (US)

(*) Notice: Subject to any disclaimer, the term of this patent is extended or adjusted under 35 U.S.C. 154(b) by 0 days.

(21) Appl. No.: 10/233,643

(22) Filed: Sep. 3, 2002

(65) Prior Publication Data

US 2003/0059403 A1 Mar. 27, 2003

Related U.S. Application Data

(62) Division of application No. 09/962,917, filed on Sep. 25, 2001, now Pat. No. 6,797,287.

(51) Int. Cl.[7] .......................... A61K 38/00; A61K 31/28
(52) U.S. Cl. .................... 514/8; 514/2; 514/6; 514/505
(58) Field of Search .................. 514/505, 783, 514/2, 6, 8; 424/195.1, 725, 757, 655, 93.4, 93.45, 93.51; 435/252.9, 254.1, 254.2, 254.21

(56) References Cited

U.S. PATENT DOCUMENTS 5,612,039 A   3/1997  Policappelli et al.

6,340,669 B1  1/2002  Cestaro et al.

FOREIGN PATENT DOCUMENTS

| DE | 26 28 757 | 12/1977 |
| DE | 0151 869 | 11/1981 |
| WO | WO 01/17369 A1 | 3/2001 |

OTHER PUBLICATIONS

Wang, J.,;Yuen, V.G.; McNeill, J.H., "Effect of vanadium on insulin sensitivity and appetite," *Metabolism* (2001) 50: 667–673.

Gary Glazer, MD, "Long–term Pharmacotherapy of Obesity 2000" *Arch Intern Med* (2001) 161: 1814–1824.

John B. Vincent, "The Biochemistry of Chromium," *American Society for Nutritional Sciences* (2000): 715–718.

Walter Mertz, "Chromium in Human Nutrition: A Review," *American Institute of Nutrition* (1993): 626–633.

*Primary Examiner*—Patricia Leith
(74) *Attorney, Agent, or Firm*—Hoffmann & Baron, LLP

(57) ABSTRACT

The present invention is for compositions containing phaseolamin and a mineral, such as chromium or vanadium or both, where the mineral is bound by a glycoprotein matrix. The present invention is also directed to methods for controlling carbohydrate cravings, inducing weight loss, reducing insulin requirements in a diabetic, and inhibiting the absorption of dietary starch by administering a composition of the invention.

25 Claims, 1 Drawing Sheet

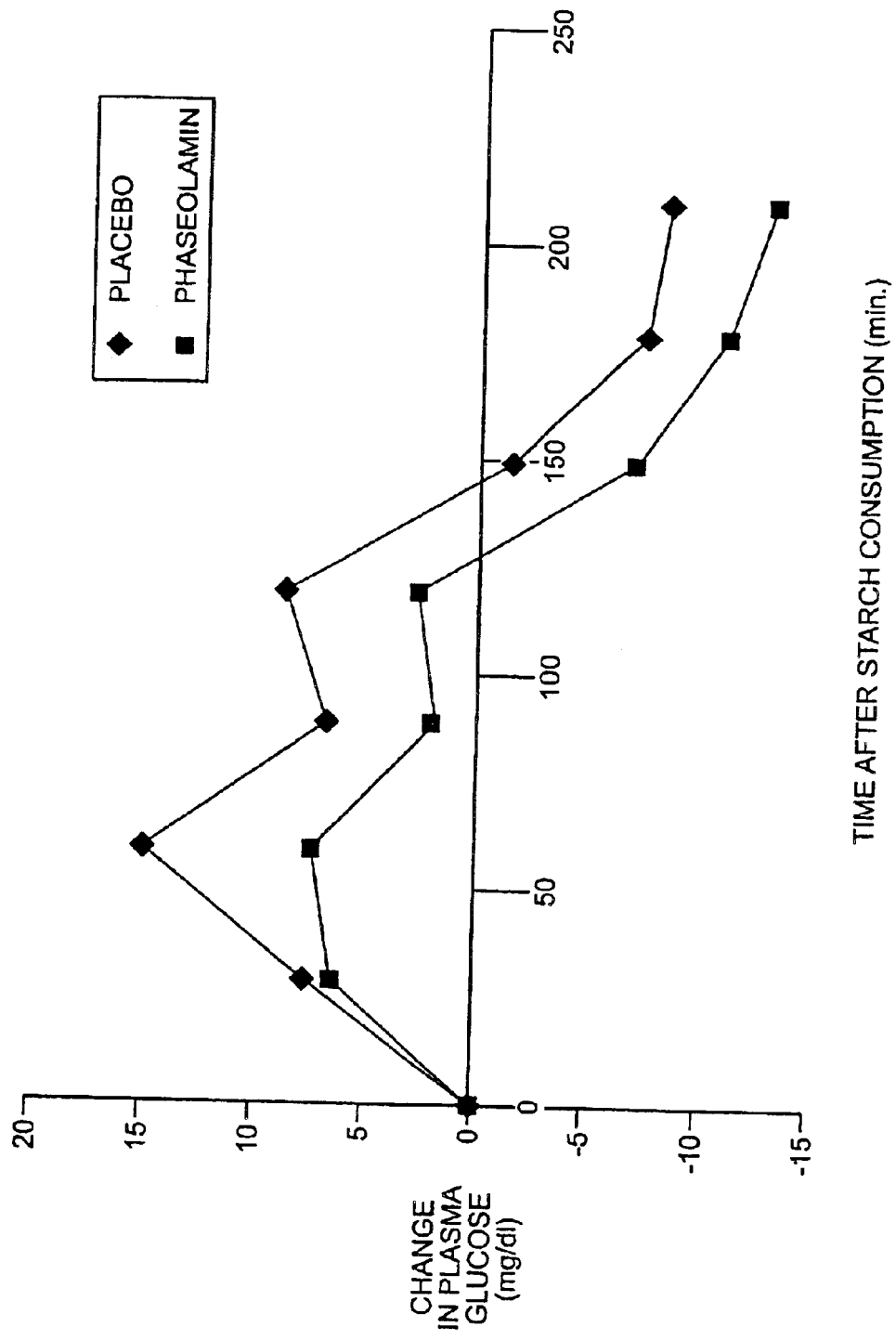
FIG. 1  EFFICACY OF PHASEOLAMIN

PHASEOLAMIN COMPOSITIONS AND METHODS FOR USING THE SAME

The present application is a divisional of, and claims priority to, U.S. application Ser. No. 09/962,917, filed Sep. 25, 2001 now U.S. Pat. No. 6,797,287.

BACKGROUND OF THE INVENTION

Glycoproteins (glycosylated proteins) are organic compounds composed of both a protein and a carbohydrate joined together by a covalent linkage. Glycosylated proteins are present on extracellular matrices and cellular surfaces of many cells. Oligosaccharides consist of a few covalently linked monosaccharide units, such as glucose and ribulose. The oligosaccharide moieties of glycoproteins are implicated in a wide range of cell-cell and cell-matrix recognition events.

The addition of carbohydrates such as oligosaccharides, on a protein involves a complex series of reactions that are catalyzed by membrane-bound glycosyltransferases and glycosidases. Glycosyltransferases are enzymes that transfer sugar groups to an acceptor, such as another sugar or a protein. Glycosidases are enzymes that remove sugar groups. The types and amounts of sugars that are attached to a given protein depend on the cell type in which the glycoprotein is expressed. In addition, the types of linkage used to join various sugar groups together also confound the complexity of glycosylation.

The biological activities of many glycoproteins are not detectably different if the carbohydrates are removed. However, glycosylation of proteins may have several effects. Carbohydrates often lengthen the biological life of a protein by decreasing the protein's rate of clearance from the blood. In addition, carbohydrates may help a protein to fold properly, stabilize a protein, or affect physical properties such as solubility or viscosity of a protein.

Phaseolamin is a glycoprotein found mainly in white and red kidney beans and is known to be an amylase inhibitor. Amylase is an enzyme responsible for the breakdown or digestion of starch. Starch is the main source of carbohydrates in the human diet. The digestion of starch begins in the mouth. Alpha-amylase present in saliva randomly hydrolyzes the $\alpha(1 \rightarrow 4)$ glucosidic bonds of starch except for the outermost bonds and those next to branches.

By the time the thoroughly chewed food reaches the stomach, the average chain length of starch is reduced from several thousand to less than eight glucose units. The acid level in the stomach inactivates the alpha-amylase. Further digestion of starch continues in the small intestine by pancreatic alpha-amylase, which is similar to that of salivary alpha-amylase.

Decreasing the absorption of carbohydrates by inhibiting the digestion of starch is a very promising strategy in the fields of, for example weight loss and diabetes mellitus. From a dietary standpoint, it is important to target the breakdown of starch since starch is a relatively nonessential nutrient, which provides calories with fairly little benefit. Furthermore, as starch is broken down into simple sugars and absorbed from the digestive tract, the pancreas is triggered to produce insulin. Increase in insulin production causes an individual to feel hunger.

Several clinical studies, however, demonstrated that commercially available crude bean amylase inhibitors, when given with a starch meal, failed to influence fecal calorie excretion, postprandial concentrations of plasma glucose or breath hydrogen, and metabolism of $^{13}$C-labeled starch. In addition, administration of amylase inhibitors has been associated with side effects, such as abdominal discomfort and diarrhea.

It is estimated that approximately 40% of the United States population suffer from obesity (Glazer, G. (2001) Arch. Intern. Med. 161:1814–1824). Obesity has been associated with many illnesses, such as cardiovascular disease, respiratory illness including asthma, sleep apnea, pickwichian syndrome, diabetes mellitus and pulmonary hypertension. In addition, adenocarcinoma of the esophagus and gastric cardia (Lagergren, J. et al. (1999) Ann. Intern. Med. 130:883–890), hepatic necrosis, and cirrhosis (Ratziu, V. et al. (2000) Gastroenterology 118:1117–1123) have recently shown strong correlation with obesity.

Approximately 90% of all obese individuals who try to lose weight fail. One reason is that the majority of obese individuals are reluctant to give up eating certain foods, including starches (i.e., pasta, bread, and potatoes). Therefore, a dietary supplement that effectively inhibits the digestion and breakdown of starch, without harmful side effects, will be beneficial in helping these individuals achieve weight loss.

In addition to assisting weight loss, inhibiting the digestion or breakdown of starch may also be beneficial in illnesses such as, for example, diabetes mellitus. Currently, between 120 and 140 million people worldwide suffer from diabetes mellitus and by the year 2025, it is estimated that this number may double. Much of the increase in individuals suffering from diabetes mellitus will occur in developing countries due to population aging, unhealthy diets, obesity, and a sedentary lifestyle.

Diabetes mellitus is a chronic disease characterized by a deficiency in the production of insulin by the pancreas, or by ineffectiveness of the insulin produced to utilize glucose. This impairment in glucose utilization results in increased concentrations of glucose in the blood, which leads to damage of many of the body's systems, such as the blood vessels and nerves. Therefore, preventing the breakdown of starch into smaller sugar units, such as glucose, will be beneficial in the prevention and/or treatment of diabetes mellitus.

Numerous articles have been published concerning amylase inhibition. Some of these articles have indicated that amylase-inhibitors worked well in vitro, but failed to be effective in humans. Some of the proffered reasons were 1) insufficient activity; 2) destruction in the gastrointestinal tract; 3) suboptimal pH conditions; and 4) differing gastric emptying rates of starch and inhibitor.

Previous attempts to block starch absorption have failed for many reasons including the instability of the starch-blockers employed. Thus, there remains a need for a stable, inhibitor of starch digestion with enhanced bioactivity and decreased side effects.

SUMMARY OF THE INVENTION

The present invention is for a composition comprising phaseolamin and a mineral, where the mineral is bound by a glycoprotein matrix. In one embodiment, the mineral is chromium or vanadium or both. In another embodiment, the composition also comprises microorganisms. In yet another embodiment, the microorganisms produce the glycoprotein matrix.

In a preferred embodiment, the microorganisms include yeast, such as Saccharomyces cervisiae. In another embodiment, the microorganisms include bacteria such as Lactobacillus, including Lactobacillus acidophillus or Bac-

*terium bifidus.* In yet another embodiment, the microorganisms include both yeast and bacteria.

In one aspect of the invention, the composition also comprises stabilizers and/or additives. In another aspect, the composition is added to a baking mix such as pancake, waffle, bread, biscuit and cookie mix.

The present invention is also directed to a method for inhibiting absorption of dietary starch in a host. The method comprises administering to a host, an effective amount of a composition comprising phaseolamin and a mineral, such as, for example, chromium or vanadium or both. The mineral is bound by a glycoprotein matrix.

In one aspect of the invention a method for inducing weight loss in a host in need thereof is provided. The method comprises administering an effective amount of a composition comprising phaseolamin and a mineral, such as, for example, chromium or vanadium. The mineral is bound by a glycoprotein matrix.

In another aspect of the invention, a method for controlling carbohydrate cravings in a host in need thereof is provided. The method comprising administering an effective amount of a composition comprising phaseolamin and a mineral, such as, for example, chromium or vanadium or both. The mineral is bound by a glycoprotein matrix.

In a final embodiment, a method for decreasing insulin requirements in a diabetic host is provided. The method comprises administering to the host, an effective amount of a composition comprising phaseolamin and a mineral, such as, for example, chromium or vanadium or both. The mineral is bound by a glycoprotein matrix.

BRIEF DESCRIPTION OF THE FIGURE

FIG. 1. Efficacy of Phaseolamin

The efficacy of phaseolamin was compared in two groups, one receiving a starch-meal(placebo), the other receiving a starch meal plus phaseolamin. The plasma glucose levels of the two groups were compared. The group receiving the phaseolamin had markedly lower plasma glucose levels during the time after the starch meal was consumed.

DETAILED DESCRIPTION OF THE INVENTION

In accordance with the present invention, a composition is provided which includes phaseolamin and a mineral, wherein the mineral is bound to a glycoprotein matrix. The composition of the invention provides improved stability and bioactivity characteristics of the mineral, in conjunction with the starch inhibition properties of phaseolamin.

The glycoprotein matrix of the present invention is bound to at least one mineral. The glycoprotein matrix and mineral can be associated with each other physically and/or chemically, such as by chemical reaction, and/or secondary chemical bonding, e.g., Van der Waals forces, etc. Not being bound by theory, it is believed that the glycoprotein matrix may be bound to the mineral by weak covalent bonds.

The composition can contain essentially any percentage of mineral and phaseolamin as desired. For example, the percentage of mineral can vary between 0.1 and 99% by weight of the composition depending upon the mineral and the desired result in the host. The percentage of phaseolamin can vary between 0.1 and 99% by weight of the composition depending upon desired result in the host.

Glycoprotein Matrix

The glycoprotein matrix is the glycoprotein to which the mineral is bound. Glycoprotein is a composite material made of a carbohydrate group and a simple protein. A glycoprotein matrix is a molecular network comprised of a plurality of glycoprotein molecules bound together.

The carbohydrate in the glycoprotein can be any suitable carbohydrate, such as a monosaccharide, disaccharide, oligosaccharide, or polysaccharide. Oligosaccharide is preferred. The protein of the glycoprotein can be any suitable polypeptide. The ratio of carbohydrate to protein in the glycoprotein matrix can vary, for example, from 99:1 to 1:99 by weight. A ratio of approximately 1:1 is preferred.

The ratio of glycoprotein matrix to mineral can also vary. It is preferred that the ratio of glycoprotein matrix to mineral will be such that all or nearly all of the mineral in the composition is bound by glycoprotein matrix. To ensure that essentially all of the mineral is bound, higher ratios of glycoprotein matrix to mineral can be used.

The invention also contemplates a composition where there may be insufficient glycoprotein to bind the entire amount of the mineral. In such cases, the ratio of glycoprotein matrix to mineral can be less.

In a preferred embodiment, the source of the glycoprotein matrix is a microorganism and, therefore, a preferred composition of the invention will include microorganisms. At the end of the manufacturing process of the composition, these microorganisms are usually inactive.

The glycoprotein matrix can be bound to the mineral by allowing the microorganism to ferment, in the presence of the mineral. As used herein, fermentation is the process by which microorganisms metabolize raw materials, such as amino acids and carbohydrate, to produce glycoprotein.

The microorganisms produce glycoprotein both intracellularly and extracellularly The intracellular glycoprotein will mainly be located in the cytoplasm of the microorganism or become part of the microorganism's physical structure. The glycoprotein from the microorganism that forms the glycoprotein matrix is mainly extracellular and, therefore, is available to be bound to the mineral. Intracellular glycoprotein can also be made accessible for binding to the mineral by rupture of the microorganisms after glycoprotein production.

Microorganisms that produce a glycoprotein matrix include, but are not limited to, yeast and some bacteria. A preferred yeast is *Saccharomyces cervisiae.* Bacteria that produce glycoprotein include bacteria within the genus *Lactobacillus.* For example, such bacteria include, but are not limited to, *Lactobacillus acidophillus, Lactobacillus bulgaricus, Lactobacillus caucasicus,* and *Bacterium bifidus.* Preferred bacteria include *Lactobacillus acidophillus,* and *Bacterium bifidus.*

Combinations of microorganisms can be used provided that at least one of the microorganisms produces glycoprotein. When using combinations of microorganisms, the growth of one type of microorganism should not prevent the growth of the other. For example, various types of different yeast that produce glycoprotein can be used. Also, yeast and bacteria can be combined to produce glycoprotein. This combination is particularly advantageous because various types of bacteria, such as *Lactobacillus acidophillus,* also produce glycoprotein.

Stabilizers and Additives

The composition of the invention can also include stabilizers and/or additives. Stabilizers and additives can include, for example, pharmaceutically acceptable buffers, excipients, diluents, surfactants, adjuvants, flavorings, and the like. The amounts of such additives can be determined by one skilled in the art.

Additives can also include, for example, natural sources of the active ingredient to be administered. Other additives can be added which, for example, improve the viability of the microorganisms that produce the glycoprotein or increase the yield of glycoprotein that becomes bound to the active ingredient. For example, salts can be added in order to increase the viability of the microorganism. Such salts include, but are not limited to, calcium carbonate, ammonium sulfate, and magnesium sulfate. Calcium carbonate is preferred. The amount of salt added to the microorganism solution should be sufficient to obtain the desired result of improving the viability of the organism, as is known in the art. A preferred range of salt added to the microorganism solution is between about 25 to about 150 grams of salt per 375 grams of microorganism, such as *Saccharomyces cervisiae*. Approximately 40 g of salt per 375 gram of microorganism is most preferred.

The composition of the invention can be manufactured so as to be biocompatible. Since the mineral is to be ingested, the microorganism used to produce the glycoprotein matrix should be suitable for consumption by mammals, especially humans. Examples of such microorganisms include *Lactobacillus acidophillus* and *Saccharomyces cervisiae*. The mineral can also include pharmaceutically acceptable buffers, excipients, diluents, adjuvants, flavorings, and the like.

Minerals

The compositions of the present invention also include a mineral. A mineral suitable for a composition of the present invention can be any mineral that is beneficial to a host. Preferred minerals are those that aid in controlling dietary starch absorption and/or carbohydrate cravings, such as, for example, vanadium and chromium.

Vanadium is an ultratrace element that is a potent nonselective inhibitor of protein tyrosine phosphatases. Vanadium has been shown to mimic many of the metabolic actions of insulin both in vivo and in vitro. For the purposes of this invention, vanadium may be naturally occurring, semisynthetic or synthetic. Preferably, the vanadium is bound by a glycoprotein matrix to form a complex.

Chromium is an essential trace element that has been shown to improve the efficiency of insulin and control dietary starch absorption and carbohydrate cravings. For the purposes of this invention, chromium can be naturally occurring, semisynthetic or synthetic. Preferably, the chromium is bound by a glycoprotein matrix to form a complex.

Phaseolamin

Phaseolamin is derived from *Phaseolus vulgaris*, or the white kidney bean. The primary function of phaseolamin is to cause temporary, safe, side-effect free malabsorption of dietary starch. Not being bound by theory, it is believed that phaseolamin binds and neutralizes alpha-amylase. By neutralizing alpha-amylase, absorption of the carbohydrate is inhibited. As will be discussed below, phaseolamin is effective for inducing weight loss, Alpha-amylase is a naturally occurring starch enzyme that is responsible for the breakdown of starches. For example, in humans, dietary starches must be broken down into smaller components, for example, glucose, in order to be utilized by the body.

Therefore, by neutralizing the body's enzyme that breaks down starches into usable components, the body is unable to use those starches and ultimately excretes them. In addition, starches that are not broken down into smaller components, such as glucose, do not trigger the production of insulin.

Amylase is a digestive tract enzyme that breaks down starch into small units capable of being further degraded into glucose which is used as fuel for normal metabolism and body homeostasis. Clinical use of inhibitors of amylase has widespread appeal because a reduction of starch digestion will influence carbohydrate uptake in individuals in need thereof.

Not being bound by theory, it is believed that in a composition of the present invention, the phaseolamin acts synergistically with both the vanadium and chromium glycoprotein complexes to enhance the effects of the phaseolamin, vanadium and chromium.

Insulin is a hormone naturally produced by the body that is key to controlling blood glucose levels. Circulating blood caries glucose that provides fuel for the cells. Getting glucose into the cells requires insulin, which is produced in the pancreas by beta cells. Normally, the pancreas produces just enough insulin to handle the body's needs. This is not the case with diabetics, as will be discussed below.

Carbohydrate consumption causes an abnormal rise in insulin. Excess insulin triggers hunger and cravings, creating a vicious cycle. One way to end the cycle is to reduce or eliminate the intake of carbohydrates. This approach has had very little or no success in inducing weight loss for the long term. It is also extremely difficult for individuals with impairment of glucose utilization, such as diabetes mellitus, to restrict their intake of carbohydrates.

The compositions of the present invention induce weight loss by inhibiting the absorption of carbohydrate. In addition, the compositions control cravings associated with carbohydrate absorption. By inhibiting absorption if dietary starch and controlling cravings associated with carbohydrate absorption, the compositions of the present invention are effective in inducing weight loss.

In addition, the compositions of the invention reduce the amount of insulin required by an individual suffering from diabetes mellitus. Accordingly, as will be discussed below, phaseolamin is an effective and beneficial treatment for overweight, obese and/or morbidly obese individuals and for individuals suffering from diabetes mellitus.

Dietary Starch

Dietary starch is any consumable starch and is a mixture of glucans (polymers of glucose). Some examples of dietary starch sources include pasta, rice, grains, potatoes and cereals. In accordance with the present invention, dietary starch is composed of, for example, amylose and/or amylopectin.

Amylose is an essentially unbranched polymer of $\alpha$-glucose residues which are joined by 1–4 glycosidic linkages. There can be about 1000 glucose residues per amylose molecule. Amylose forms a helical coil structure and is only slightly soluble in water due to the internal —OH groups. Amylopectin is a highly branched polymer of $\alpha$-glucose residues. Amylopectin usually consists of about 20–25 glucose residues.

Other types of dietary starch include, for example, cellulose, pectin, hydrocolloids or gums and maltodextrins. Consumption of dietary starch has been linked to weight gain, diabetes mellitus, and various gastrointestinal conditions including, for example, irritable bowel syndrome.

Dosage and Administration

The glycoprotein matrix compositions containing a mineral can be administered topically or systemically. Systemic administration can be enteral or parenteral. Enteral administration is preferred. For example, the compositions can easily be administered orally. Liquid or solid (e.g., tablets, gelatin capsules) formulations can be employed. The formulation can include pharmaceutically acceptable excipients, adjuvants, diluents, or carriers.

The compositions can be administered in chewable tablet granulations, with or without sugar, in powdered drink mixes, chewing gum and baking products. In a preferred embodiment, because the compositions are stable under baking temperatures, the compositions are effectively administered in baking mixes such as pancakes, waffles, breads, biscuits or cookies.

In accordance with the present invention, an effective amount of a claimed composition is any amount known to those skilled in the art. Preferably, an effective amount is administered to a host just prior to, during or shortly after consuming a starch-rich meal.

Host

In a preferred embodiment the host is a mammal. Mammals include, for example, humans, as well as pet animals such as dogs and cats, laboratory animals such as rats and mice, and farm animals such as horses and cows. Humans are most preferred.

A host in need of weight loss is, for example, any host where the weight of the host is not beneficial for its health. Another example of a host in need of weight loss is, for example, a host that is unhappy with it's appearance due to excess weight. Some examples of hosts in need of weight loss include, but are not limited to, hosts that suffer from diabetes mellitus and overweight individuals.

A host is considered overweight when the body weight of the mammal is greater than the ideal body weight according to the height and body frame of the host. The ideal body weight of a host is known to those skilled in the art. A host is considered in need of weight loss if its body weight is at least about 10%, preferably at least about 30%, more preferably at least about 60%, and most preferably at least about 100% greater than their ideal body weight.

A host, for example, a human, is considered obese when its body weight is increased beyond the limitation of skeletal and physical requirement as the result of excessive accumulation of fat in the body. Obesity can be the result of many different forces, such as, for example, overeating or a medical condition. A medical condition that could result in obesity is, for example, a low metabolic rate.

Morbid obesity occurs when an individuals weight is two, three or four times the ideal weight for that individual, and is so-called because it is associated with many seriously life-threatening disorders.

Many different approaches have been advanced for the treatment of overweight, obese and/or morbidly obese individuals with little success and great side-effects. The present invention provides a novel resolution which will effectively aid in inducing weight loss. The claimed composition comprising phaseolamin and a mineral bound by a glycoprotein matrix is effective in blocking starch absorption and controlling carbohydrate cravings.

The claimed composition comprising phaseolamin and a mineral, such as vanadium or chromium or both, bound by a glycoprotein matrix will provide inhibition the absorption of starch and control carbohydrate cravings.

The composition of the invention may also be used in a mammal suffering from an impairment of glucose utilization, for example, diabetes mellitus. The impairment in glucose utilization may occur as a result of a deficiency in the production of insulin by the pancreas, or by ineffectiveness of the insulin produced to utilize glucose. As discussed above, insulin is necessary to the transport of glucose from the blood into cells.

In diabetes mellitus, insulin is either absent, in short supply or unable to perform its job efficiently. If glucose cannot get into the cells, it accumulates in the blood creating increased blood glucose.

All clinicians recognize that dietary factors play a role in the treatment of diabetes mellitus. In many diabetic individuals, weight loss may cure or significantly improve diabetes mellitus.

A number of meal planning systems are used in conventional diabetes care settings. One of the most popular systems is carbohydrate counting which involves maintaining a relatively constant level of carbohydrates from day to day. By doing so, the insulin needs of the diabetic individual are more or less predictable and constant.

Individuals suffering from diabetes mellitus usually need to ingest insulin to aid in the absorption of blood glucose into cells. Often, after consuming a carbohydrate rich meal, a diabetic's insulin requirements may markedly increase to deal with the high blood glucose levels.

Accordingly, by inhibiting the absorption of dietary starch, a composition of the present invention will effectively decrease the insulin requirements of a diabetic host.

The following examples are provided to assist in a further understanding of the invention. The particular materials and conditions employed are intended to be further illustrative of the invention and are not limiting upon the reasonable scope thereof.

EXAMPLE 1

Preparation of Mineral+Glycoprotein Matrix (GPM) Complex

This example demonstrates the preparation of a mineral (i.e., chromium or vanadium) plus glycoprotein matrix (GPM) complex to yield a mineral+GPM complex. The method employs preparing, in a first container, an aqueous solution of USP inorganic mineral salt and adding a peptone made of amino acids.

In a second container an active yeast solution is prepared. Active baker's yeast, *Saccharomyces cervisiae* added to water to form an aqueous solution. Maltose and gum acacia are then added.

The first container containing the mineral is then inoculated very slowly into the active yeast solution to form a live fermented solution. The mixture is allowed to ferment for four to six hours. To promote yeast growth, plant proteins and carbohydrates are added Proteolytic enzyme, such as papain, is then added.

*Lactobacillus acidophillus* is added to the live fermented solution and allowed to ferment for about 2 hours. Active fermentation is then stopped by heating the solution to 160–170° F. for three hours.

The fermented mineral solution is then homogenized in a shearing pump (Charles Ross & Sons Corp.) for approximately 1–2 hours and spray dried (NIRO, Nicholas Engineers Research Corp.) for approximately 4 hours. The resulting product is a powder containing the mineral GPM complex.

EXAMPLE 2

Preparation of Phaseolamin

Whole dried non-genetically modified organism (GMO) *Phaseolus vulgaris* beans were inspected for cleanliness. Upon quality control approval of the beans, the dried beans were milled and placed in a solvent, preferably water, or an alcohol-water mixture.

Phaseolamin was extracted from the bean fraction multiple times under strict standard operating procedures as are known to those in the art, such as, for example, affinity chromatography. The extracted phaseolamin was then spray dried and tested for bacterial contamination, mesh (i.e., particle size), moisture content, potency, and organoleptics (i.e., physical characteristics, such as, color, taste, odor, powder, and liquid).

EXAMPLE 3

Preparation of Phaseolamin with Mineral+GPM Complex

Phaseolamin was added to a mineral+GPM complex (obtained from Example 1) and mixed together. The resulting mixture yielded a composition comprising phaseolamin and a mineral+GPM complex. This method may be used to prepare, for example, 1) phaseolamin with chromium+GPM complex; 2) phaseolamin with vanadium+GPM complex; and 3) phaseolamin with chromium+GPM complex and vanadium+GPM complex. The methods for preparing the above listed compositions are briefly described below.

Briefly, to prepare phaseolamin with a chromium+GPM complex, 4500 mgs of phaseolamin was added to 3 mgs of chromium+GPM complex and mixed together. The resulting mixture yielded 6 µgs of elemental chromium per 4.5 g of phaseolamin.

To prepare phaseolamin with a vanadium+GPM complex, phaseolamin at 4500 mgs was added to 3 mgs of vanadium+GPM complex and mixed together. The resulting mixture yielded 6 µg of elemental vanadium per 4.5 g of phaseolamin.

To prepare phaseolamin with chromium+GPM complex and vanadium+GPM complex, 4500 mgs of phaseolamin at was added to 1.5 mgs of chromium+GPM complex and 1.5 mgs of vanadium+GPM complex and mixed together. The resulting mixture yielded 3 µg of elemental chromium and 3 µg of elemental vanadium per 4.5 g of phaseolamin.

EXAMPLE 4

Efficacy of Phaseolamin

To study the efficacy of phaseolamin, five males and five females (ages 21 to 57) participated in a double-blind placebo-controlled crossover study. All subjects were instructed to go about their usual daily routines throughout the study. After an overnight fast, the participants were sampled for blood and then given in a random manner either:

Group 1) (placebo) a starch meal consisting of 4 slices of white bread (60 grams of carbohydrate) with 42 grams of soybean oil margarine and 4 grams of Sweet N' Low spread on the bread; or Group 2) a starch meal consisting of 4 slices of white bread (60 grams of carbohydrate) with 42 grams of soybean oil margarine and 4 grams of Sweet N' Low spread on the bread; plus 1.5 grams of PHASEOLAMIN 2250™ (*phaseolus vulgaris* extract sold by PharmaChem Laboratories. Inc., Kearny, N.J.).

Plasma glucose was measured by a commercial enzyme kit (Sigma Chemical Company) from blood drawn at baseline, and every 30 minutes for 4 hours. After one week the regimen was repeated where the starch meal containing PHASEOLAMIN 2250™ was administered to the subjects group 1 and the subjects in group2 were administered the starch meal without PHASEOLAMIN 2250™.

The subjects were normoglycemic as measured by fasting glucose concentration which averaged 98 mg/dl for the placebo and 104 for the PHASEOLAMIN 2250™ starch meal. From 60 to 120 minutes after consumption of the starch meal, the change in plasma glucose of the PHASEOLAMIN 2250™ group from the baseline was ½ to ⅓ of the level of the placebo group (FIG. 1). PHASEOLAMIN 2250™ consumption caused the plasma glucose to return to baseline values 20 minutes earlier than the placebo without PHASEOLAMIN 2500™.

The average area under the plasma glucose time curve from 0 to 150 minutes, which is a measure of absorption and metabolism, was 57% lower with PHASEOLAMIN 2250™. Plotting the average change in glucose concentration from 30 minutes to 210 minutes, the area under the curve was positive for the placebo but negative for PHASEOLAMIN 2250™.

This indicates that very little of the glucose from the starch in the bread was absorbed when co-ingested with PHASEOLAMIN 2250™ and that the glucose was cleared very rapidly. No side effects were observed in subjects treated with PHASEOLAMIN 2250™.

I claim:

1. A method for inhibiting absorption of dietary starch in a host, wherein said method comprises administering to said host, an effective amount of a composition comprising effective amounts of phaseolamin and chromium, wherein said chromium is bound by a glycoprotein matrix, wherein the glycoprotein matrix is a molecular network comprising a plurality of glycoproteins bound together, and wherein the glycoproteins are produced by *Lacrobacillus acidophilus* and *Saccharomyces cervisiae*.

2. A method according to claim 1, wherein said composition further comprises stabilizers and/or additives.

3. A method according to claim 1, wherein said dietary starch is amylose.

4. A method according to claim 1, wherein said host is a human.

5. A method according to claim 4, wherein said human is obese.

6. A method according to claim 4, wherein said human is morbidly obese.

7. A method according to claim 4, wherein said human suffers from an impairment of glucose utilization.

8. A method according to claim 1, wherein said composition is administered in a baked good.

9. A method according to claim 8, wherein said baked good is selected from the group consisting of pancake, waffle, bread, biscuit and cookie.

10. A method for inducing weight loss in a host in need thereof, said method comprising administering an effective amount of a composition comprising effective amounts of phaseolamin and chromium, wherein said chromium is bound by a glycoprotein matrix, wherein the glycoprotein matrix is a molecular network comprising a plurality of glycoproteins bound together, and wherein the glycoproteins are produced by *Lactobacillus acidophilus* and *Saccharomyces cervisiae*.

11. A method according to claim 10, wherein said composition further comprises stabilizers and/or additives.

12. A method according to claim 10, wherein said host is a human.

13. A method according to claim 12, wherein said human is obese.

14. A method according to claim 12, wherein said human is morbidly obese.

15. A method according to claim 12, wherein said human suffers from an impairment of glucose utilization.

16. A method according to claim 10, wherein said composition is administered in a baked good.

17. A method according to claim 16, wherein said baked good is selected from the group consisting of pancake, waffle, bread, biscuit and cookie.

18. A method for controlling carbohydrate cravings in a host in need thereof, said method comprising administering to said host an effective amount of a composition comprising effective amounts of phaseolamin and chromium, wherein said chromium is bound by a glycoprotein matrix, wherein the glycoprotein matrix is a molecular network comprising a plurality of glycoproteins bound together, and wherein the glycoproteins are produced by *Lactobacillus acidopizilus* and *Saccharomyces cervisiae*.

19. A method according to claim 18, wherein said composition further comprises stabilizers and/or additives.

20. A method according to claim 18, wherein said host is a human.

21. A method according to claim 20, wherein said human is obese.

22. A method according to claim 20, wherein said human is morbidly obese.

23. A method according to claim 20, wherein said human suffers from an impairment of glucose utilization.

24. A method according to claim 18, wherein said composition is administered in a baked good.

25. A method according to claim 24, wherein said baked good is selected from the group consisting of pancake, waffle, bread, biscuit and cookie.

* * * * *

UNITED STATES PATENT AND TRADEMARK OFFICE
CERTIFICATE OF CORRECTION

PATENT NO. : 6,900,174 B2
DATED : May 31, 2005
INVENTOR(S) : Chokshi

It is certified that error appears in the above-identified patent and that said Letters Patent is hereby corrected as shown below:

Column 11,
Line 16, now reads "acidopizilus and" should read -- acidphilus and --.

Signed and Sealed this

Eighth Day of November, 2005

JON W. DUDAS
*Director of the United States Patent and Trademark Office*